United States Patent [19]

Kataoka et al.

[11] Patent Number: 4,458,018

[45] Date of Patent: Jul. 3, 1984

[54] PROCESS FOR PURIFYING ELASTASE

[75] Inventors: Tsunehiko Kataoka, Kakamigahara; Yoshiaki Nagara, Hajima; Akera Hashemoto, Kakamigahara; Masayuki Konishi, Tchenomiya; Koichi Ogawa, Inazawa, all of Japan

[73] Assignee: Eisai Co., Ltd., Tokyo, Japan

[21] Appl. No.: 446,079

[22] Filed: Dec. 1, 1982

[30] Foreign Application Priority Data

Dec. 15, 1981 [JP] Japan .............................. 56-200856

[51] Int. Cl.$^3$ ............................................. C12N 9/66
[52] U.S. Cl. .................................... 435/218; 435/814
[58] Field of Search ............................... 435/218, 814

[56] References Cited

U.S. PATENT DOCUMENTS 4,071,410 1/1978 Yoshizawa .

OTHER PUBLICATIONS

Lewis et al., Journal of Biological Chemistry, vol. 256, pp. 705-720, (1956).
Methods in Enzymology, vol. 19, pp. 113-140, (1970).

Primary Examiner—Lionel M. Shapiro
Attorney, Agent, or Firm—Flynn, Thiel, Boutell & Tanis

[57] ABSTRACT

A process is disclosed for purifying elastase by precipitating elastase from an aqueous, elastase-containing solution, in which the electroconductivity of said aqueous solution is adjusted to 3 millimhos per centimeter or less and the pH of the solution is adjusted to a value of from 2 to 5. The electroconductivity of said aqueous solution is preferably adjusted to 3 millimhos per centimeter or less by means of ultrafiltration.

10 Claims, 1 Drawing Figure

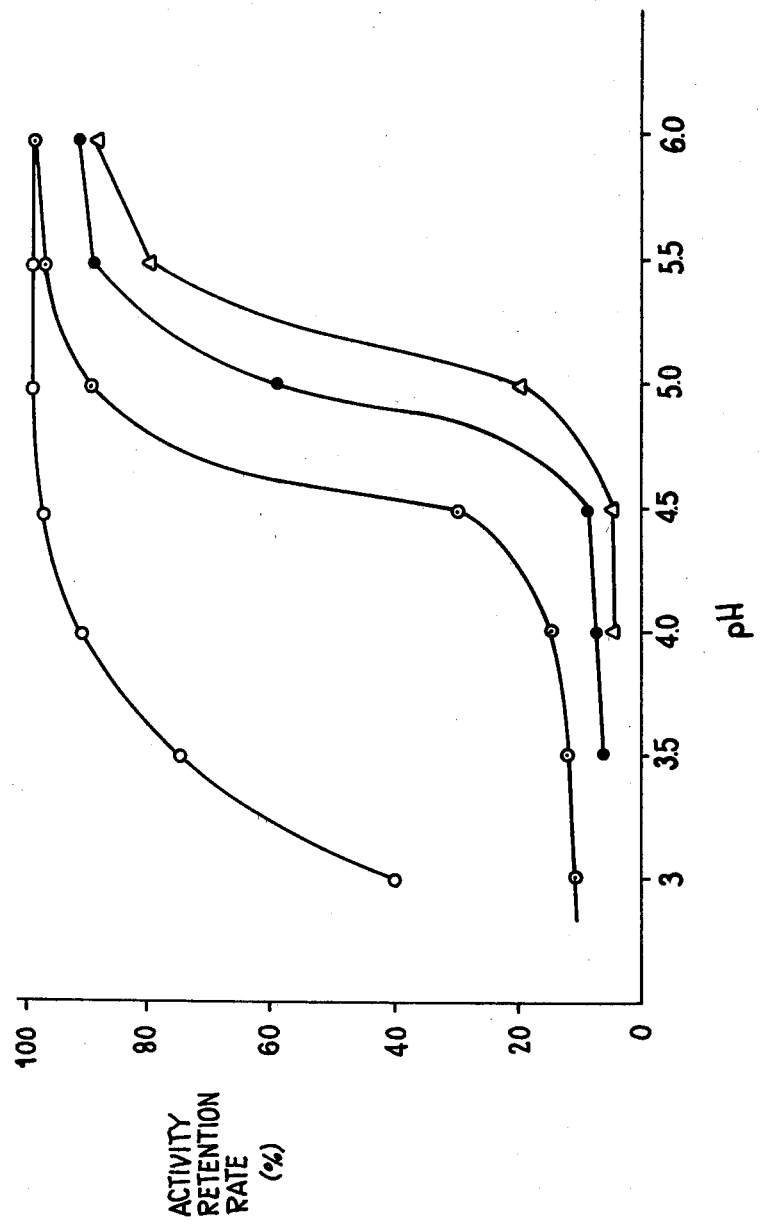

PROCESS FOR PURIFYING ELASTASE

This invention relates to a process for purifying elastase. More particularly, the invention relates to a process for purifying elastase by precipitating elastase from an aqueous, elastase-containing solution, in which the electroconductivity of the aqueous, elastase-containing solution is adjusted to 3 millimhos per centimeter (m$\Omega$/cm) or lower and the pH thereof is adjusted to a value in the range of 2 to 5. The object of the invention is to obtain elastase as a high-activity elastase fraction by adjusting the electroconductivity and pH of the aqueous, elastase-containing solution within the above-defined ranges.

For the preparation of elastase, there has been generally employed a process according to which an elastase precursor contained in swine pancreas is first separated and activated by a suitable method and then is subjected to ammonium sulfate fractionation (salting out) or treatment with an organic solvent, whereby to obtain a crude elastase-containing product. Elastase in this crude product is then extracted by adding thereto a phosphate buffer or the equivalent, and the thus-extracted elastase is subjected to further ammonium sulfate fractionation and then is crystallized.

This conventional process involves various problems, particularly in the stage of purifying elastase contained in the crude elastase-containing product. For example, in this stage, a large volume of ammonium sulfate must be used or else the elastase activity of the obtained ammonium sulfate fractionation product will be low because of the low amount of ammonium sulfate consumed for the purification, which means that a large amount of elastase which is contaminated with impurities still remains in the precipitate. Thus, in the art of purification of elastase, a method for obtaining a high-activity elastase fraction from a crude, elastase-containing product, by a simple and easy operation, is still being pursued.

The present invention has been completed based on the discovery that elastase can be purified by a simple and easy operation by regulating the electroconductivity and the pH of an aqueous, elastase-containing solution within certain respective defined ranges in the crystallization stage.

BRIEF DESCRIPTION OF THE DRAWING

The drawing is a graph showing the relationship between the pH and the elastase activity retention rates of samples of crude elastase-containing solutions as determined using four sample solutions of different electroconductivities.

DETAILED DESCRIPTION OF THE INVENTION

The aqueous, elastase-containing solution used as a starting material in this invention can be an aqueous solution obtained at any stage after an elastase precursor, for example, an elastase precursor contained in the pancreas of a mammal, has been activated to convert it to elastase. For example, such a solution can be prepared by dissolving, in water or a phosphate buffer, a crude elastase-containing product obtained by extracting crude elastase after the activation thereof and then treating the crude extract with an organic solvent, or it can be a filtrate obtained by clarifying and filtering such an aqueous solution containing elastase.

One of the essential requirements of the process of this invention is that the electroconductivity of the aqueous, elastase-containing solution is kept at 3 millimhos per centimeter or lower. Various techniques, such as ultrafiltration, ion exchange or reverse osmosis, can be employed for complying with this requirement. Among these techniques, ultrafiltration is the most suitable for the purposes of this invention. As will be apparent from the experimental results described below, when the electroconductivity is above 3 millimhos per centimeter, the precipitation rate of elastase is poor and it is thus difficult to prepare an elastase fraction possessing high elastase activity.

Another requirment for the process of this invention is that the pH of the crude, aqueous, elastase-containing solution is maintained within the range of 2 to 5. This requirement can be met by adding a suitable amount of acetic acid, hydrochloric acid or a similar acid to the aqueous, elastase-containing solution. Acetic acid is particularly preferred for the purposes of this invention. The experimental results given below show that elastase precipitation progresses rapidly at a pH of 5 or below, and that the most desirable results are obtained when the pH is 3 to 4.5.

More specifically, the preferred process of this invention comprises subjecting an aqueous, elastase-containing solution to ultrafiltration, then adding thereto an acid, preferably acetic acid, to adjust the electroconductivity and pH of the crude, aqueous, elastase-containing solution to within the specified ranges, thereby making it possible to recover most of the elastase initially present in the starting aqueous solution, for example, 90% or more, as a high-activity elastase precipitate. Thus, when the process of this invention is practiced, the amount of residual elastase that remains in the starting aqueous solution is very small, e.g., less than 10% of the amount of elastase that was initially present in the starting solution. Generally, when the electroconductivity of the solution is high, the pH should be lower. For example, when the electroconductivity is about 1.2 millimhos per centimeter, the solution should be adjusted to a pH of 4.8 or lower, but when the electroconductivity is about 2 millimhos per centimeter, it is desirable to keep the pH below 4.5. Likewise, when the electroconductivity is about 3 millimhos per centimeter, the pH should preferably be 3 or lower. However, an excessively low pH may cause denaturation of the elastase, so that it is usually desirable to keep the pH of the solution above 2.

When the elastase precipitate obtained according to the process of this invention is immediately filtered and dried in vacuo, the desired elastase material can be obtained as a dry product. When further purified elastase crystals are required, a purification method, such as disclosed in Japanese Patent Publication No. 21557/1975, can be employed. According to this method, an elastase precipitate, such as the one obtained according to the process of this invention, is filtered and redissolved in an aqueous solution to form, for example, an elastase solution of pH 7. This solution is allowed to stand and the elastase crystals which precipitate therefrom are centrifuged and freeze-dried. This purifying method is generally used when elastase of especially high purity is required. Such a treatment is unnecessary when the elastase precipitate obtained by the process of this invention can be used without further purification for a particular use. The present invention does not require the use of such an additional purification method.

The invention will be further described in the following experimental example.

Experimental Example

Specimens and test method

A crude elastase-containing product obtained as described in Example 1 was dissolved in 10 times as much water by volume and the solution was clarified and filtered to prepare samples of an aqueous, elastase-containing solution.

These samples were subjected to ultrafiltration so that the separate samples had electroconductivities of 5, 3, 2 and 1.2 millimhos per centimeter, respectively. Then concentrated acetic acid was added to the samples to adjust the pH of different samples to several different levels. After the samples and a sample of the starting aqueous solution were left standing for one hour after the pH adjustment as described above, and then removing the elastase precipitates, the elastase activities of the residual solutions were measured to determine the activity retention rate for each sample.

Results

The results are shown in the drawing, which illustrates the relation between the pH and the activity retention rate (%) of the residual solutions of the respective samples. In the drawing, the curves with data points marked with open circles (O), dotted circles ( ), closed circles ( ), and triangles (Δ) represent samples having electroconductivities of 5, 3, 2 and 1.2 millimhos per centimeter, respectively. It is observed from the drawing that the activity retention rates of the elastase in the aqueous, elastase-containing sample solutions sharply decreases, thus indicating, by difference, that a high yield of elastase is obtained in the precipitates, when the electroconductivity of the aqueous solution is 3 millimhos per centimeter or lower and the pH of the solution is 5 or lower, preferably 4.5 or lower.

The present invention will now be described in further detail in the following illustrative examples.

Example 1

To 1 kg of minced swine pancreas there were added 200 ml of water, 7 g of pancreatin and then 5 ml of a 40% aqueous solution of sodium hydroxide. The mixture was stirred vigorously and then allowed to stand at 17° C. for 2 hours to activate the elastase in the mixture. Acetone was added to the activated mixture to prepare a solution having a concentration of 70 V/V% and the solution was stirred for one hour. The acetone was removed and then 1.2 l of water was added to the resulting precipitate to form a solution and the solution was stirred for 2 hours. After addition of 10 g of Hyflo Super Cel, the solution was subjected to crude filtration. The resulting 1.8 l of the filtrate was diluted with acetone to a concentration of 60 V/V% and the precipitate thus formed was filtered. The precipitate was further washed three times with 1.5 l portions of acetone and then dried in vacuo to obtain a crude elastase-containing product.

To 50 g of this crude product was added 500 ml of water to form a solution and, after 2 hours, the solution was clarified and filtered to obtain 500 ml of an aqueous, elastase-containing solution. This solution was further subjected to ultrafiltration to remove components having molecular weights of lower than 10,000, and to obtain 100 ml of a concentrated elastase-containing solution, which solution was then diluted with water to obtain 500 ml of solution. The electroconductivity of this dilute solution was 1.6 millimhos per centimeter. Its pH was then adjusted to 4.5 by adding 1.0 ml of concentrated acetic acid thereto. After allowing the solution to stand for one hour, the precipitate formed was filtered out, then the precipitate was dissolved in water again to form an aqueous solution of pH 7.0, and was allowed to stand for 3 days. The crystals formed at the end of this time were removed by centrifuging and then freeze-dried to obtain 1.2 g of elastase crystals having an elastin decomposition activity of 150 units/mg.

Example 2

To 10 kg of minced swine pancreas there were added 10 l of water, 70 g of pancreatin and then 50 ml of a 40% aqueous solution of sodium hydroxide. The mixture was stirred and then left standing at 35° C. for 2 hours to effect elastase activation. This solution was then diluted with acetone to a concentration of 30 V/V%, and after addition of 100 g of Hyflo Super Cel, the solution was subjected to crude filtration. The resulting crude filtrate was diluted with acetone to a concentration of 60 V/V%, and the precipitate thereby formed was filtered out. The precipitate was then further washed three times with 15 l portions of acetone and dried in vacuo to obtain a crude elastase-containing product. To 100 g of this crude product 1 l of water was added to form a solution, and after 2 hours the solution was clarified and filtered to obtain 1 l of a crude, aqueous, elastase-conntaining solution. This solution was subjected to ultrafiltration to remove components having molecular weights of lower than 10,000, thereby to obtain 150 ml of a concentrated solution, to which water was added to make 1 l of an aqueous solution. The electroconductivity of this solution was 1.2 millimhos per centimeter. Its pH was adjusted to 4.5 by adding 2 ml of concentrated acetic acid thereto. After the solution was allowed to stand for one hour, the formed precipitate was filtered out, dissolved again in water to form an aqueous solution of pH 7.0, and allowed to stand for 3 days. The crystals formed at the end of this period were centrifuged and then freeze-dried to obtain 2.5 g of elastase crystals having an elastin decomposition activity of 150 units/mg.

We claim:

1. A process for purifying elastase which comprises treating a starting aqueous solution of crude elastase to obtain a modified aqueous solution having an electroconductivity of not greater than 3 millimhos per centimeter and a pH of from 2 to 5, and then precipitating elastase from said modified aqueous solution.

2. A process according to claim 1, wherein the electroconductivity of said starting solution is adjusted to 3 millimhos per centimeter or below by effecting ultrafiltration of said starting solution.

3. A process according to claim 1, wherein the pH of said modified aqueous solution is in the range of 3 to 4.5.

4. A process according to claim 1, in which said starting aqueous solution is prepared by extracting an elastase precursor from mammalian pancreas, then mixing said elastase precursor with an activating agent under conditions effective to activate said precursor to form a crude elastase product, then recovering said crude elastase product and forming said starting aqueous solution therefrom.

5. A process according to claim 1, wherein the electroconductivity of said modified aqueous solution is about 1.2 millimhos per centimeter and the pH of said modified aqueous solution is 4.8 or lower.

6. A process according to claim 1, wherein the electroconductivity of said modified aqueous solution is about 2 millimhos per centimeter and the pH of said modified aqueous solution is 4.5 or lower.

7. A process according to claim 1, wherein the electroconductivity of said modified aqueous solution is about 3 millimhos per centimeter and the pH of said solution is 3 or lower.

8. A process according to claim 4, wherein said mammalian pancreas is porcine pancreas.

9. A process for preparing elastase comprising
   (a) extracting an elastase precursor from mammalian pancreas;
   (b) then mixing said elastase precursor with an activating agent under conditions effective to activate said precursor to form elastase;
   (c) then recovering said elastase in the form of an impure, solid, elastase-containing product;
   (d) then adding water to said solid elastase-containing product to form a crude, aqueous, elastase-containing solution;
   (e) then subjecting said crude, aqueous, elastase-containing solution to ultra-filtration whereby to remove therefrom impurities having molecular weights of 10,000 or lower and to obtain a modified, aqueous, elastase-containing solution having an electroconductivity of 3 millimhos per centimeter or less;
   (f) then adding acetic acid to said modified solution to adjust the pH of said modified solution to be in the range of 2 to 5;
   (g) then allowing said solution to stand for a time sufficient to form a precipitate of elastase; and
   (h) then recovering said precipitate.

10. A process according to claim 9, wherein the pH of said solution after said acetic acid addition is in the range of 3 to 4.5.

* * * * *